US012595221B1

(12) United States Patent
Giles et al.

(10) Patent No.: US 12,595,221 B1
(45) Date of Patent: Apr. 7, 2026

(54) HYDROFORMYLATION PROCESSES

(71) Applicant: Dow Technology Investments LLC, Midland, MI (US)

(72) Inventors: Jason F. Giles, Missouri City, TX (US); Glenn A. Miller, South Charleston, WV (US)

(73) Assignee: Dow Technology Investments LLC, Midland, MI (US)

( * ) Notice: Subject to any disclaimer, the term of this patent is extended or adjusted under 35 U.S.C. 154(b) by 456 days.

(21) Appl. No.: 18/261,417

(22) PCT Filed: Feb. 23, 2022

(86) PCT No.: PCT/US2022/017496
§ 371 (c)(1),
(2) Date: Jul. 13, 2023

(87) PCT Pub. No.: WO2022/211930
PCT Pub. Date: Oct. 6, 2022

Related U.S. Application Data

(60) Provisional application No. 63/168,483, filed on Mar. 31, 2021.

(51) Int. Cl.
*C07C 45/50* (2006.01)

(52) U.S. Cl.
CPC .................................... *C07C 45/50* (2013.01)

(58) Field of Classification Search
CPC ............................... C07C 45/50; B01J 10/002
See application file for complete search history.

(56) References Cited

U.S. PATENT DOCUMENTS

| | | | |
|---|---|---|---|
| 4,148,830 | A | 4/1979 | Pruett et al. |
| 4,262,142 | A | 4/1981 | Sherman, Jr. et al. |
| 4,277,627 | A | 7/1981 | Bryant et al. |
| 4,523,036 | A | 6/1985 | Cornils et al. |
| 4,717,775 | A | 1/1988 | Billig et al. |
| 4,769,498 | A | 9/1988 | Billig et al. |
| 5,237,106 | A | 8/1993 | Babin et al. |
| 5,362,917 | A | 11/1994 | Ogawa et al. |
| 5,367,106 | A | 11/1994 | Unruh et al. |
| 5,728,893 | A | 3/1998 | Becker et al. |
| 5,741,945 | A | 4/1998 | Bryant et al. |
| 5,744,650 | A | 4/1998 | Nicholson et al. |
| 5,763,678 | A | 6/1998 | Beckers et al. |
| 5,763,679 | A | 6/1998 | Nicholson et al. |
| 5,767,321 | A | 6/1998 | Billig et al. |
| 7,446,231 | B2 | 11/2008 | Peterson et al. |
| 7,863,487 | B2 | 1/2011 | Eisenschmid et al. |
| 7,906,688 | B2 | 3/2011 | Brammer et al. |
| 8,389,774 | B2 | 3/2013 | Becker et al. |
| 8,598,390 | B2 | 12/2013 | Eisenschmid et al. |
| 8,664,451 | B2 | 3/2014 | Eisenschmid et al. |
| 9,670,122 | B2 | 6/2017 | Smith et al. |
| 9,688,598 | B2 | 6/2017 | Eisenschmid et al. |
| 9,695,098 | B2 * | 7/2017 | Miller ..................... C07C 45/50 |

FOREIGN PATENT DOCUMENTS

| | | |
|---|---|---|
| CN | 101293818 | 10/2008 |
| CN | 101565353 | 10/2009 |
| CN | 102030622 | 4/2011 |
| CN | 103130623 | 6/2013 |
| DE | 10035370 | 3/2001 |
| KR | 101060353 | 8/2011 |
| RU | 2561171 | 8/2015 |
| WO | 2012/008717 | 1/2012 |
| WO | 2015094781 | 6/2015 |
| WO | 2015094813 | 6/2015 |

OTHER PUBLICATIONS

Falbe, "Potential Industrial Significance", New Syntheses with Carbon Monoxide, 1980, pp. 18-21.
Van Elk, "Modelling of gas—liquid reactors—stability and dynamic behavior of a hydroformylation reactor, influence of mass transfer in the kinetics controlled regime", Chemical Engineering Science, 2001, vol. 56, pp. 1491-1500.
PCT/US2022/017496 International Search Report and Written Opinion with a mailing date of Jun. 3, 2022.

* cited by examiner

*Primary Examiner* — Sikarl A Witherspoon

(57) ABSTRACT

This disclosure relates to continuous hydroformylation processes. In one aspect, a continuous hydroformylation process comprises: (a) contacting CO, $H_2$, and at least one olefin in the presence of a hydroformylation catalyst in a reaction fluid in at least two reaction zones under hydroformylation conditions sufficient to form at least one aldehyde product, wherein the hydroformylation catalyst comprises a catalytic metal and a ligand and wherein a reaction temperature in the first reaction zone is controlled using a first heat exchanger; and (b) recovering at least a portion of the hydroformylation catalyst from a product stream and recycling at least a portion of the recovered hydroformylation catalyst through the first reaction zone. The heat evolution in the first reaction zone is reduced by reducing the reaction rate in the first reaction zone and increasing the reaction rate in a downstream reaction zone to insure sufficient heat removal capacity remains on the heat exchanger in the first reaction zone to insure stable control of the reaction at a target reaction temperature.

8 Claims, 1 Drawing Sheet

HYDROFORMYLATION PROCESSES

FIELD

The present invention relates generally to continuous hydroformylation processes.

INTRODUCTION

It is known that aldehydes can be produced by a continuous process comprising reacting an olefinically unsaturated compound with carbon monoxide and hydrogen in the presence of a metal-organophosphorus ligand complex catalyst. This process is disclosed in, e.g., U.S. Pat. Nos. 4,148,830; 4,717,775; and 4,769,498. Reaction temperature is an important hydroformylation process variable for several reasons.

It is generally recognized that steady and controlled operation of a commercial-scale hydroformylation plant is highly desirable. It is also clear that accurate temperature control is critical to catalyst life. The problem of temperature control in hydroformylation reactions on a commercial scale has long been recognized. In section 1.2.4 in J. Falbe (ed) "New Syntheses with Carbon Monoxide" (Springer-Verlag, NY 1980) a summary of the problem with a diagram of erratic temperature behavior is shown. A more detailed analysis is given in E. P. Van Elk, P. C. Borman, J. A. M. Kuipers, G. F. Versteeg; *Chemical Engineering Science* 56 (2001) 1491-1500) where the complications of stability and dynamic behavior are discussed. Rhodium hydroformylation reactions are characterized by complex kinetics, mass flow issues, and their very exothermic (28-35 kcal (118-147 kJ)/mol olefin) nature, all of which make temperature control quite difficult.

U.S. Pat. No. 4,277,627 teaches several routes of catalyst deactivation including intrinsic deactivation. Operating conditions are specified to minimize the loss of activity with phosphine-based catalysts. Temperature is a key variable that controls the rate of catalyst deactivation.

In addition to its effect on catalyst stability, controlling the temperature can have a significant impact on the efficiency of the process. Lower temperatures give lower reactivity and result in lost olefin through the system. Higher temperatures give higher ligand decomposition and heavies formation rates due to inevitable aldol formation, as taught in U.S. Pat. No. 4,148,830. Other temperature-related effects, such as higher hydrogenation (to alkane or alcohol) and variation of the normal-to-branched ("N:I") product ratio, may also negatively impact plant productivity.

Generally speaking, to control the temperature, one must control the rate of heat generation and/or the rate of heat removal. At steady state, these two are equal. The rate of heat generation generally will be determined by factors such as the desired plant production rate (i.e., olefin feed rate), the nature of the olefin (ethylene being highly reactive followed by primary then secondary olefins), and catalyst concentration, to name a few. The production rate and olefin used are generally not changed due to the resulting negative impact on plant economics. Therefore, historically most of the focus for temperature control has been on heat removal.

The removal of heat from a heat exchanger is traditionally described by the following equation:

$$\text{Heat Removal}=A*U*\Delta T \tag{1}$$

where "U" is a heat transfer coefficient dependent on the conditions on both the process and coolant side of the equipment (viscosity, sensible heat, flow rates, presence of bubbles, etc.), "A" is the surface area available for the heat transfer, and ΔT is the temperature difference between the product fluid and the coolant.

The surface area of the exchanger is generally a constant. Large internal cooling coils inside a reactor take up valuable reactor space, so it is common practice to use external heat exchangers on reactors needing a substantial amount of heat removal. See, e.g., PCT Publication No. WO2012/008717 A2, U.S. Pat. Nos. 4,523,036, 8,389,774, and 5,367,106. Increasing the size of the heat exchanger to have a very large surface area will generally give better stability but is expensive, increases the plant footprint, and increases maintenance costs.

There are disclosures that aim at controlling the reactor temperature via manipulation of operating conditions. For example, with the highly active phosphite-based Rh catalyst systems disclosed in U.S. Pat. No. 5,744,650, optimizing the temperature difference, ΔT, between the process and coolant side of heat exchangers is critical to steady temperature control. U.S. Pat. No. 5,744,650 gives a good overview of practical heat exchanger design used to control hydroformylation reactors but focuses on the coolant side of the heat exchanger. Unfortunately, controlling the temperature of the cooling water adds complexity and expense to the plant construction and operation. It also adds considerable process control response delay, in that changes to the cooling water temperature take time, and then the altered cooling water has to re-establish a temperature at the heat exchanger, which then must establish a new ΔT to show an effect at the reactor. The large masses involved in industrial scale hydroformylation processes greatly increase the response time.

Traditionally the other means to effect heat removal is based on changing the coolant mass flow rate in the heat exchanger. Changing the flow on the coolant side has been viewed as the preferred path since the piping and equipment on the coolant side are generally much smaller than the process side, e.g., 6 inch vs. 20 inch pipes, and involve less expensive metals, e.g., carbon steel compared to stainless steel on the process side.

It is also known that reaction kinetics, which are affected by temperature, have a large impact on process stability. U.S. Pat. No. 5,763,679 teaches that deactivation of metal-organophosphorus ligand complex catalysts caused by inhibiting or poisoning phosphorus compounds can be reversed or reduced by conducting the hydroformylation process in a reaction region where the hydroformylation reaction rate is of a negative or inverse order in carbon monoxide. The presence of both positive and negative CO order kinetics (as well as varying levels of inhibitors) makes controlling these highly active catalysts very challenging using conventional process control strategies.

U.S. Pat. No. 5,362,917 discloses a method of controlling the stability of hydroformylation processes by varying the flow rate of a synthesis feed gas or the flow rate of a vent gas to maintain a predetermined constant carbon monoxide partial pressure in the hydroformylation process. Since the product isomer (N:I) ratio is dependent on the CO partial pressure, attempting to maintain the CO partial pressure may stabilize the N:I ratio but not the reaction rate at the same time, since the other reagents may be changing as well.

Similarly, U.S. Pat. No. 7,446,231 deals with controlling the reaction by manipulating the reactor total pressure. This attempts to deal simultaneously with several gaseous reagents that impact the kinetics. Instead of setting a fixed CO partial pressure, the total pressure is maintained at a constant propylene feed rate based on the observation that the CO and $H_2$ partial pressures will self-control, and the hope that a steadier process will result. As shown in FIG. 1 in U.S. Pat. No. 7,446,231, the optimal operating region is at the peak of the hydroformylation rate versus CO partial pressure plot, where the highest rate and N:I performance is observed. Unfortunately, operating at this peak is inherently unstable since kinetic models do not account for changing reaction orders (including zero order at the peak itself). Therefore, the technique of U.S. Pat. No. 7,446,231 only applies in the negative CO order region.

Thus, hydroformylation reactors typically operate in an inherently unstable regime and depend on the reactor control system to maintain stable process control. Conventional hydroformylation reactor temperature control systems have adjusted the cooling water inlet temperature, cooling water flow rate, or a combination of these to control the reactor liquid temperature. Historically, this control scheme has worked reasonably well, primarily because the first generation, commercial hydroformylation catalysts had relatively low reaction rates, e.g., less than 1.5 gmoles aldehyde/liter reactor volume/hr, which generated relatively low reaction heat per unit time/volume. However, recently commercialized next-generation hydroformylation catalysts have significantly higher reaction rates compared to prior catalysts. The higher reaction rates result in higher heat generation in the hydroformylation reactor per unit time. The conventional reactor temperature control scheme is too slow for effective reactor temperature control of reactions that use the new hydroformylation catalysts.

The design of heat exchangers is well known in the art and the issues discussed above are to be taken into account in the design of the heat exchanger to insure it has sufficient capacity to remove the heat generated in the system at the rate it is generated including the variations described above. The term "capacity" as used herein in connection with heat exchangers is the maximum amount of thermal energy (often measured in BTUs, kiloJoules, kilowatts, etc.) the heat exchanger can remove per unit time when operated at its maximum heat removal mode. As noted in Equation (1) above, there are a number of factors that impact the heat removal rate thus the heat exchanger capacity such as U, A, and ΔT. Generally the process or coolant flows (U) and ΔT (coolant temperature) are the primary factors for capacity. These must be balanced against the amount of heat generated by the hydroformylation reaction plus some additional capacity to deal with variations such as olefin purity, cooling water variation (e.g., seasonal variations), and the like. It is assumed that the hydroformylation production rate (total olefin feed) is kept constant such that the plant production rate is constant.

It has been found that conventional heat exchanger designs can become inadequate over time, especially with higher activity catalysts and/or more highly reactive olefins. Examples include dramatic changes in olefin composition in the feed, fouling, and change in catalyst activity. The latter is especially of concern when an older facility is retrofitted with a more active catalyst such as described above. The higher activity catalyst converts more of the olefin in the first reactor than the older, less active catalysts which means more heat generation is occurring in the first reactor than in the original plant design. The older designs typically lack the rapid response needed for negative order catalsysts as well. Simply lowering the reactor temperature to reduce the reaction rate also lowers the ΔT across the heat exchanger, reducing the heat exchanger capacity as well. Since the new highly reactive catalysts tend to be more sensitive to higher temperatures and are run at lower temperatures yet still exhibit higher olefin conversion, this effect magnifies the heat exchanger capacity limitations. To mitigate the problem would require replacement of the existing heat exchanger or the addition of further cooling capacity which is expensive and increases plant footprint and maintenance costs.

It would therefore be desirable to have an improved reactor temperature control process for hydroformylation reactors that balances heat removal needs of the reactor with the use of existing heat exchangers having limited heat removal capacity.

SUMMARY

The present invention generally relates to continuous hydroformylation processes that provide improved heat reactor temperature control. In some aspects, the continuous hydroformylation processes are particularly advantageous with processes using active hydroformylation catalysts that generate more heat in the reactor than traditional hydroformylation catalysts. In some aspects, such processes can facilitate the use of heat exchangers to sufficiently remove heat from reactors using newer, active hydroformylation catalysts when such heat exchangers having a heat removal capacity designed for reactions with traditional hydroformylation catalysts. For example, some embodiments of continuous hydroformylation processes of the present invention can be useful in converting hydroformylation processes operating with certain hydroformylation catalysts (e.g., traditional catalysts) to processes using more active (more highly reactive) hydroformylation catalysts without having to replace the heat exchanger(s) associated with the hydroformylation reactor.

In one embodiment, a continuous hydroformylation process of the present invention comprises: (a) contacting CO, $H_2$, and at least one olefin in the presence of a hydroformylation catalyst in a reaction fluid in at least two reaction zones under hydroformylation conditions sufficient to form at least one aldehyde product, wherein the hydroformylation catalyst comprises a catalytic metal and a ligand and wherein a reaction temperature in the first reaction zone is controlled using a first heat exchanger; and (b) recovering at least a portion of the hydroformylation catalyst from a product stream and recycling at least a portion of the recovered hydroformylation catalyst through the first reaction zone, wherein the heat evolution in the first reaction zone is reduced by reducing the reaction rate in the first reaction zone and increasing the reaction rate in a downstream reaction zone to insure sufficient heat removal capacity remains on the heat exchanger in the first reaction zone to insure stable control of the reaction at a target reaction temperature by: (1) diverting a portion of an olefin feed stream to a reaction zone downstream from the first reaction zone and changing the olefin partial pressure pressure in the first reaction zone by adjusting the amount of the olefin feed stream that is diverted; and/or (2) diverting a portion of the recycled hydroformylation catalyst to a reaction zone downstream from the first reaction zone and changing the concentration of the catalytic metal in the first reaction zone by adjusting the amount of the recycled hydroformylation catalyst that is diverted.

These and other embodiments are described in more detail in the Detailed Description.

DETAILED DESCRIPTION

Figure 1:
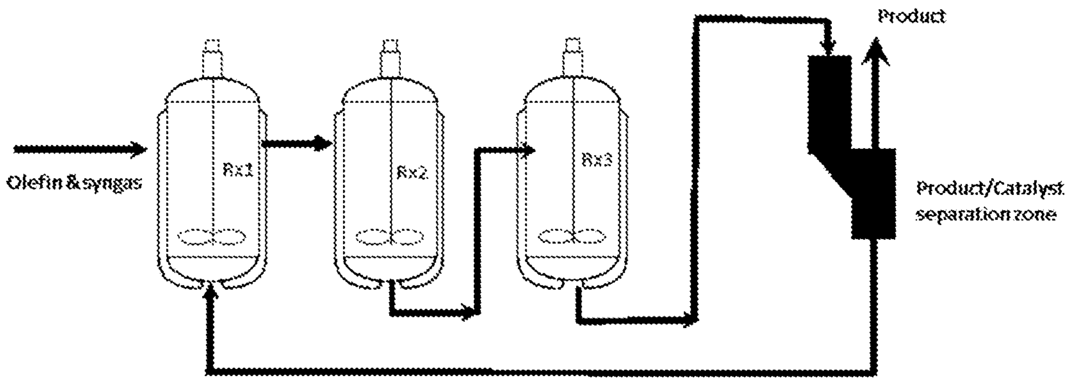
FIG. 1 is a process flow sheet showing a conventional reaction train with three reactors (reaction zones) in series feeding into a product/catalyst separation zone where crude product is removed and the catalyst is recycled back to the first reactor.

This disclosure relates generally to reducing the heat evolution in a first reaction zone in a continuous hydroformylation process by reducing the reaction rate in the first reaction zone and increasing the reaction rate in a downstream reaction zone to insure sufficient heat removal capacity remains on the heat exchanger in the first reaction zone to insure stable control of the reaction at a target reaction temperature. The processes described herein are continuous ones for producing aldehydes by the hydroformylation of alpha-olefins. Aldehydes produced by such processes have a wide range of utility, for example, as intermediates for hydrogenation to aliphatic alcohols, for amination to aliphatic amines, for oxidation to aliphatic acids, and for aldol condensation to produce plasticizers.

All references to the Periodic Table of the Elements and the various groups therein are to the version published in the CRC Handbook of Chemistry and Physics, 72nd Ed. (1991-1992) CRC Press, at page I-10.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc.

As used herein, the term "ppmw" means part per million by weight.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds that can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxyalkyl, aminoalkyl, in which the number of carbons can range from 1 to 20 or more, preferably from 1 to 12, as well as hydroxy, halo, and amino. The permissible substituents can be one or more and the same or different for appropriate organic compounds. This invention is not intended to be limited in any manner by the permissible substituents of organic compounds.

As used herein, the term "hydroformylation" is contemplated to include, but not limited to, all permissible asymmetric and non-asymmetric hydroformylation processes that involve converting one or more substituted or unsubstituted olefinic compounds or a reaction mixture comprising one or more substituted or unsubstituted olefinic compounds to one or more substituted or unsubstituted aldehydes or a reaction mixture comprising one or more substituted or unsubstituted aldehydes.

The terms "reaction fluid," "reaction medium" and "catalyst solution" are used interchangeably herein, and may include, but are not limited to, a mixture comprising: (a) a metal-organophosphorous ligand complex catalyst, (b) free organophosphorous ligand, (c) aldehyde product formed in the reaction, (d) unreacted reactants, (e) a solvent for said metal-organophosphorous ligand complex catalyst and said free organophosphorous ligand, and, optionally, (f) one or more ligand degradation products such as oxides or phosphorus acidic compounds formed in the reaction (which may be homogeneous or heterogeneous, and these compounds include those adhered to process equipment surfaces). The reaction fluid can encompass, but is not limited to, (a) a fluid in a reaction zone, (b) a fluid stream on its way to a separation zone, (c) a fluid in a separation zone, (d) a recycle stream, (e) a fluid withdrawn from a reaction zone or separation zone, (f) a withdrawn fluid being treated with an aqueous buffer solution, (g) a treated fluid returned to a reaction zone or separation zone, (h) a fluid in an external cooler, and (i) ligand decomposition products and their salts.

As used herein, the terms "reactor" and "reaction zone" refer to a distinct unit or units wherein the conditions are such that the hydroformylation reaction is occurring. These conditions comprise the presence of olefin, syngas, and catalyst in solution at sufficiently high temperature that detectable amounts of heat is generated. The terms "reactor" and "reaction zone" are used interchangeably except when a reactor body has multiple zones in which case the term "reaction zone" will be expressly employed (e.g., the second reaction zone within a single reactor body). The reaction zone may encompass more than one reactor in series or may be a reactor with several separate reaction zones or stages within the reactor body such as described in U.S. Pat. No. 5,728,893. The terms "downstream reaction zone" or "downstream reactor" are used interchangeably herein to refer to the main process flow of the reaction train wherein the first reaction zone where the olefin is first charged to the reaction zone series and wherein the product of this reaction zone is then fed to the second (downstream) reaction zone, which is then fed to the third reaction zone (if present) and so on until the final reaction zone in the series is then connected to the product/catalyst separation zone.

"Hydrolyzable organophosphorous ligands" are trivalent phosphorous ligands that contain at least one P—Z bond wherein Z is oxygen, nitrogen, chlorine, fluorine or bromine. Examples include, but are not limited to, phosphites, phosphino-phosphites, bisphosphites, phosphonites, bisphosphonites, phosphinites, phosphoramidites, phosphino-phosphoramidites, bisphosphoramidites, fluorophosphites, and the like. The ligands may include chelate structures and/or may contain multiple P—Z moieties such as polyphosphites, polyphosphoramidites, etc. and mixed P—Z moieties such as phosphite-phosphoramidites, flurophosphite-phosphites, and the like.

The term "complex" as used herein means a coordination compound formed by the union of one or more electronically rich molecules or atoms (i.e., ligand) with one or more electronically poor molecules or atoms (i.e., transition metal). For example, the organophosphorous ligand employable herein possesses one phosphorus (III) donor atom having one unshared pair of electrons, which is capable of forming a coordinate covalent bond with the metal. A polyorganophosphorous ligand employable herein possesses two or more phosphorus (III) donor atoms, each having one unshared pair of electrons, each of which is capable of forming a coordinate covalent bond independently or possibly in concert (for example, via chelation) with the transition metal. Carbon monoxide can also be present and complexed with the transition metal. The ultimate composition of the complex catalyst may also contain an additional ligand(s) such as described above, for example, hydrogen, mono-olefin, or an anion satisfying the coordination sites or nuclear charge of the metal.

The number of available coordination sites on the transition metal is well known in the art and depends upon the particular transition metal selected. The catalytic species may comprise a complex catalyst mixture of monomeric, dimeric or higher nuclearity forms, which forms preferably are characterized by at least one organophosphorus-containing molecule complexed per one molecule of metal, for example, rhodium. For instance, it is considered that the catalytic species of the preferred catalyst employed in the hydroformylation reaction may be complexed with carbon monoxide and hydrogen in addition to one or more organophosphorous ligand(s).

In one embodiment, a continuous hydroformylation process of the present invention comprises (a) contacting CO, $H_2$, and at least one olefin in the presence of a hydroformylation catalyst in a reaction fluid in at least two reaction zones under hydroformylation conditions sufficient to form at least one aldehyde product, wherein the hydroformylation catalyst comprises a catalytic metal and a ligand and wherein a reaction temperature in the first reaction zone is controlled using a first heat exchanger; and (b) recovering at least a portion of the hydroformylation catalyst from a product stream and recycling at least a portion of the recovered hydroformylation catalyst through the first reaction zone. In such an embodiment, the heat evolution in the first reaction zone is reduced by reducing the reaction rate in the first reaction zone and increasing the reaction rate in a downstream reaction zone to insure sufficient heat removal capacity remains on the heat exchanger in the first reaction zone to insure stable control of the reaction at a target reaction temperature by: (1) diverting a portion of an olefin feed stream to a reaction zone downstream from the first reaction zone and changing the olefin partial pressure pressure in the first reaction zone by adjusting the amount of the olefin feed stream that is diverted; and/or (2) diverting a portion of the recycled hydroformylation catalyst to a reaction zone downstream from the first reaction zone and changing the concentration of the catalytic metal in the first reaction zone by adjusting the amount of the recycled hydroformylation catalyst that is diverted. In some embodiments, the reaction temperature in the first reaction zone is maintained within 1° C. of the target reaction temperature. Some processes of the present invention further comprise measuring the olefin concentration in a headspace of the first reaction zone and adjusting the amount of the olefin feed stream diverted to the downstream reaction zone based on the measurement. In some embodiments, the reaction rate is greater than 1.5 gmoles aldehyde/liter reactor volume/hour. In some embodiments, the reaction rate is greater than 2.0 gmoles aldehyde/liter reactor volume/hour. The ligand used in the hydroformylation reaction, in some embodiments, is a hydrolyzlable organophosphorus ligand. In some embodiments, the catalytic metal is rhodium. In some embodiments, the reaction temperature is 100° C. or less.

As noted above, hydroformylation processes of the present invention comprise contacting CO, $H_2$, and at least one olefin in the presence of a hydroformylation catalyst in a reaction fluid in at least two reaction zones under hydroformylation conditions sufficient to form at least one aldehyde product, wherein the hydroformylation catalyst comprises a catalytic metal and a ligand. Optional process components include an amine and/or water such as described in U.S. Pat. Nos. 5,288,918, 5,731,472, and 5,741,944.

Hydrogen and carbon monoxide may be obtained from any suitable source, including petroleum cracking and refinery operations. Syngas mixtures are a preferred source of hydrogen and CO.

Syngas (from synthesis gas) is the name given to a gas mixture that contains varying amounts of hydrogen ($H_2$) and carbon monoxide (CO). Production methods are well known. Hydrogen and CO typically are the main components of syngas, but syngas may contain $CO_2$ and inert gases such as $N_2$ and Ar. The molar ratio of $H_2$ to CO varies greatly but generally ranges from 1:100 to 100:1 and preferably between 1:10 and 10:1. Syngas is commercially available and is often used as a fuel source or as an intermediate for the production of other chemicals. The most preferred $H_2$:CO ratio is between 3:1 and 1:3 and more preferably is from about 1:2 to 2:1.

The substituted or unsubstituted olefinic unsaturated reactants that may be employed in the hydroformylation process include both optically active (prochiral and chiral) and non-optically active (achiral) olefinic unsaturated compounds containing from 2 to 40 carbon atoms in some embodiments, 3 to 20 carbon atoms in some embodiments, and 3 to 5 carbon atoms in some embodiments. Such compounds are well-known in the art and described in detail in US Patent Publication No. 2010/006980. Such olefinic unsaturated compounds can be terminally or internally unsaturated and be of straight-chain, branched chain or cyclic structures, as well as olefin mixtures, such as obtained from the oligomerization of propene, butene, isobutene, etc. (such as so called dimeric, trimeric or tetrameric propylene and the like, as disclosed, for example, in U.S. Pat. Nos. 4,518,809 and 4,528,403).

Prochiral and chiral olefins useful in the asymmetric hydroformylation that can be employed to produce enantiomeric aldehyde mixtures include those represented by the formula:

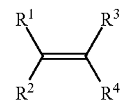

wherein $R^1$, $R^2$, $R^3$ and $R^4$ are the same or different (provided that $R^1$ is different from $R^2$ or $R^3$ is different from $R^4$) and are selected from hydrogen; alkyl; substituted alkyl, said substitution being selected from dialkylamino such as benzylamino and dibenzylamino, alkoxy such as methoxy and ethoxy, acyloxy such as acetoxy, halo, nitro, nitrile, thio, carbonyl, carboxamide, carboxaldehyde, carboxyl, and carboxylic ester; aryl including phenyl; substituted aryl including phenyl, said substitution being selected from alkyl, amino including alkylamino and dialkylamino such as benzylamino and dibenzylamino, hydroxy, alkoxy such as methoxy and ethoxy, acyloxy such as acetoxy, halo, nitrile, nitro, carboxyl, carboxaldehyde, carboxylic ester, carbonyl, and thio; acyloxy such as acetoxy; alkoxy such as methoxy and ethoxy; amino including alkylamino and dialkylamino such as benzylamino and dibenzylamino; acylamino and diacylamino such as acetylbenzylamino and diacetylamino; nitro; carbonyl; nitrile; carboxyl; carboxamide; carboxaldehyde; carboxylic ester; and alkylmercapto such as methylmercapto. It is understood that the prochiral and chiral olefins of this definition also include molecules of the above general formula where the R groups are connected to form ring compounds, e.g., 3-methyl-1-cyclohexene, and the like.

Illustrative optically active or prochiral olefinic compounds useful in asymmetric hydroformylation are described, for example, in U.S. Pat. Nos. 4,329,507, 5,360,938 and 5,491,266.

In some embodiments, mixtures of olefins may be used and the composition of this mixture may change with time. As the composition of the olefin mixture changes, the reactivity of the hydroformylation step can likewise change, sometimes rapidly. For example, changing from a polymer-grade propylene feed to a refinery-grade feed propylene feed having a substantial ethylene content can result in dramatic changes in the reaction system behavior.

A solvent advantageously is employed in the hydroformylation process. Any suitable solvent that does not unduly interfere with the hydroformylation process can be used. By way of illustration, suitable solvents for rhodium catalyzed hydroformylation processes include those disclosed, for example, in U.S. Pat. Nos. 3,527,809; 4,148,830; 5,312,996; and 5,929,289. Non-limiting examples of suitable solvents include saturated hydrocarbons (alkanes), aromatic hydrocarbons, water, ethers, aldehydes, ketones, nitriles, alcohols, esters, and aldehyde condensation products. Specific examples of solvents include: tetraglyme, pentanes, cyclohexane, heptanes, benzene, xylene, toluene, diethyl ether, tetrahydrofuran, butyraldehyde, and benzonitrile. The organic solvent may also contain dissolved water up to the saturation limit. Illustrative preferred solvents include ketones (e.g., acetone and methylethyl ketone), esters (e.g., ethyl acetate, di-2-ethylhexyl phthalate, 2,2,4-trimethyl-1,3-pentanediol monoisobutyrate), hydrocarbons (e.g., toluene), nitrohydrocarbons (e.g., nitrobenzene), ethers (e.g., tetrahydrofuran (THF)) and sulfolane. In rhodium catalyzed hydroformylation processes, it may be preferred to employ, as a primary solvent, aldehyde compounds corresponding to the aldehyde products desired to be produced and/or higher boiling aldehyde liquid condensation by-products, for example, as might be produced in situ during the hydroformylation process, as described for example in U.S. Pat. Nos. 4,148,380 and 4,247,486. The primary solvent will normally eventually comprise both aldehyde products and higher boiling aldehyde liquid condensation by-products ("heavies"), due to the nature of the continuous process. The amount of solvent is not especially critical and need only be sufficient to provide the reaction medium with the desired amount of transition metal concentration. Typically, the amount of solvent ranges from about 5 percent to about 95 percent by weight, based on the total weight of the reaction fluid. Mixtures of solvents may be employed.

The hydroformylation catalyst used in the hydroformylation process comprises a catalytic metal and a ligand. The ligand is typically an organophosphorous ligand. Illustrative metal-organophosphorous ligand complexes employable in such hydroformylation reactions include metal-organophosphorous ligand complex catalysts. These catalysts, as well as methods for their preparation, are well known in the art and include those disclosed in the patents mentioned herein. In general, such catalysts may be preformed or formed in situ and comprise metal in complex combination with an organophosphorous ligand, carbon monoxide and optionally hydrogen. The ligand complex species may be present in mononuclear, dinuclear and/or higher nuclearity forms. However, the exact structure of the catalyst is not known.

The metal-organophosphorous ligand complex catalyst can be optically active or non-optically active. The catalytic metals can include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium. Mixtures of these metals may be used. The permissible organophosphorous ligands that make up the metal-organophosphorous ligand complexes and free organophosphorous ligand include mono-, di-, tri- and higher polyorganophosphorus ligands. Mixtures of ligands may be employed in the metal-organophosphorous ligand complex catalyst and/or free ligand, and such mixtures may be the same or different.

The organophosphorous compounds that may serve as the ligand of the metal-organophosphorous ligand complex catalyst and/or free ligand may be of the achiral (optically inactive) or chiral (optically active) type and are well known in the art. Achiral organophosphorous ligands are preferred.

Among the organophosphorous ligands that may serve as the ligand of the metal-organophosphorous ligand complex catalyst are triarylphosphines, monoorganophosphite, diorganophosphite, triorganophosphite, organopolyphosphite, organomonophosphoramidite and organopolyphosphoramidite compounds and other hydrolyzable organophosphorous compounds. Such organophosphorous ligands and methods for their preparation are well known in the art.

The triarylphosphine employable in the process of this disclosure comprises any organic compound comprising one phosphorus atom covalently bonded to three aryl or arylalkyl radicals, or combinations thereof. A mixture of triarylphosphine ligands may also be employed. Representative organomonophosphines include those having the formula:

<<I>>

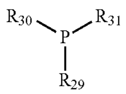

wherein each $R^{29}$, $R^{30}$ and $R^{31}$ may be the same or different and represent a substituted or unsubstituted aryl radical containing from 4 to 40 carbon atoms or greater. Such triarylphosphines may be found described in greater detail, for example, in U.S. Pat. No. 3,527,809, the disclosure of which is incorporated herein by reference. Illustrative triarylphosphine ligands are triphenylphosphine, trinaphthylphine, tritolylphosphine, tri(p-biphenyl)phosphine, tri(p-methoxyphenyl) phosphine, tri(m-chlorophenyl)-phosphine, p-N,N-dimethylaminophenyl bis-phenyl phosphine, and the like. Triphenyl phosphine, i.e., the compound of Formula I wherein each $R^{29}$, $R^{30}$ and $R^{31}$ is phenyl, is an example of a preferred organomonophosphine ligand. The hydroformylation reaction is preferentially effected in a liquid body containing excess, free triarylphosphine.

Representative monoorganophosphites, diorganophosphites, triorganophosphites, and organopolyphosphites (containing two or more tertiary (trivalent) phosphorus atoms) may include those having the following formulae that are described in detail in WO/2012/14541:

<<II>>

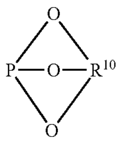

<<III>>

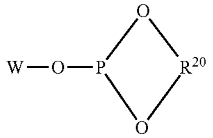

<<IV>>

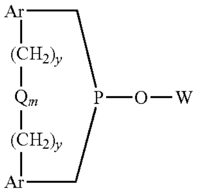

<<V>>

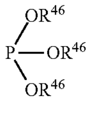

<<VI>>

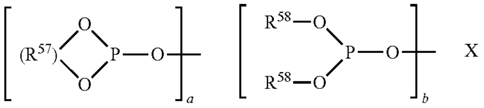

<<VII>>

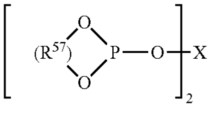

-continued

<<VIII>>

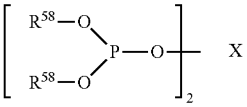

<<IX>>

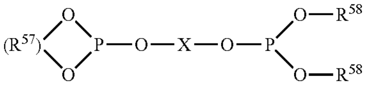

As a further option, any organophosphoramidite ligand can be used as the, or in combination with any other, organophosphorous ligand, and any organopolyphosphoramidite ligand can be used as the, or in combination with any other, organophosphorous ligand. Organophosphoramidite ligands are known, and they are used in the same manner as organophosphite ligands. Representative organophosphoramidite ligands are of formulae (X-XII).

(X)

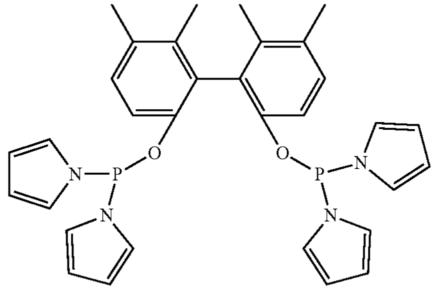

(XI)

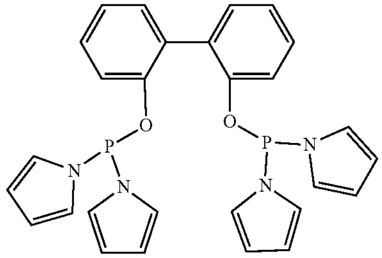

(XII)

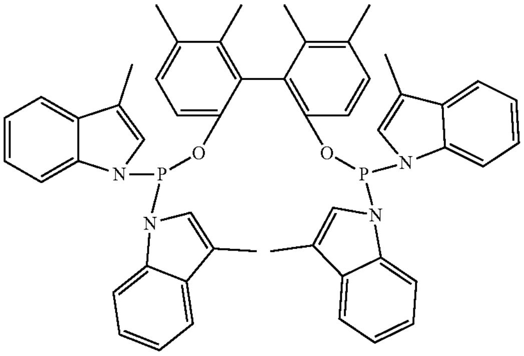

Organophosphoramidites are further described in, for example, U.S. Pat. No. 7,615,645. As here used "organophosphorous ligands" and like terms include organomonophosphoramidite and organopolyphosphoramidite ligands unless specifically noted otherwise.

Specific illustrative examples of such organophosphorous ligands include the following: 2-t-butyl-4-methoxyphenyl(3, 3'-di-t-butyl-5,5'-dimethoxy-1,1'-biphenyl-2,2'-diyl)phosphite, methyl(3,3'-di-t-butyl-5,5'-dimethoxy-1,1'-biphenyl-2,2'-diyl)phosphite, 6,6'-[[3,3'-bis(1,1-dimethylethyl)-5,5'-dimethoxy-[1,1'-biphenyl]-2,2'-diyl]bis(oxy)]bis-dibenzo[d,f][1,3,2]dioxaphosphepin, 6,6'-[[3,3',5,5'-tetrakis(1,1-dimethylethyl)-1,1'-biphenyl]-2,2'-diyl]bis(oxy)]bis-dibenzo[d,f][1,3,2]-dioxaphosphepin, (2R,4R)-di[2,2'-(3,3',5,5'-tetrakis-tert-butyl-1,1-biphenyl)]-2,4-pentyldiphosphite, (2R,4R)di[2,2'-(3,3'-di-tert-butyl-5,5'-dimethoxy-1,1'-biphenyl)]-2,4-pentyldiphosphite, 2-[[2-[[4,8,-bis(1,1-dimethylethyl), 2,10-dimethoxydibenzo-[d,f][1,3,2]dioxophosphepin-6-yl]oxy]-3-(1,1-dimethylethyl)-5-methoxyphenyl]methyl]-4-methoxy, methylenedi-2,1-phenylene tetrakis[2,4-bis(1,1-dimethylethyl)phenyl]ester of phosphorous acid, and [1,1'-biphenyl]-2,2'-diyl tetrakis [2-(1,1-dimethylethyl)-4-methoxyphenyl]ester of phosphorous acid.

The metal-organophosphorous ligand complex catalysts may be in homogeneous or heterogeneous form. For instance, preformed rhodium hydrido-carbonyl-organophosphorous ligand catalysts may be prepared and introduced into a hydroformylation reaction mixture. More preferably, the rhodium-organophosphorous ligand complex catalysts can be derived from a rhodium catalyst precursor that may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$, and the like may be introduced into the reaction mixture along with the organophosphorous ligand for the in situ formation of the active catalyst. In a preferred embodiment, rhodium dicarbonyl acetylacetonate is employed as a rhodium precursor and reacted in the presence of a solvent with the organophosphorous ligand to form a catalytic rhodium-organophosphorous ligand complex precursor that is introduced into the reactor along with excess (free) organophosphorous ligand for the in situ formation of the active catalyst. In any event, it is sufficient that carbon monoxide, hydrogen and the organophosphorous ligand are all ligands that are capable of being complexed with the metal and that an active metal-organophosphorous ligand catalyst is present in the reaction mixture under the conditions used in the hydroformylation reaction. Carbonyl and organophosphorous ligands may be complexed to the rhodium either prior to or in situ during the hydroformylation process.

By way of illustration, a preferred catalyst precursor composition consists essentially of a solubilized rhodium carbonyl organophosphorous ligand complex precursor, a solvent and, optionally, free organophosphorous ligand. The preferred catalyst precursor composition can be prepared by forming a solution of rhodium dicarbonyl acetylacetonate, an organic solvent and a organophosphorous ligand. The organophosphorous ligand readily replaces one of the carbonyl ligands of the rhodium acetylacetonate complex precursor as witnessed by the evolution of carbon monoxide gas.

Accordingly, the metal-organophosphorus ligand complex catalyst advantageously comprise the metal complexed with carbon monoxide and an organophosphorous ligand, said ligand being bonded (complexed) to the metal in a chelated and/or non-chelated fashion.

Mixtures of catalysts can be employed. The amount of metal-organophosphorous ligand complex catalyst present in the reaction fluid need only be that minimum amount necessary to provide the given metal concentration desired to be employed and that will furnish the basis for at least the catalytic amount of metal necessary to catalyze the particular hydroformylation process involved such as disclosed, for example, in the above-mentioned patents. In general, catalytic metal, e.g., rhodium, concentrations in the range of from 10 ppmw to 1000 ppmw, calculated as free metal in the reaction medium, should be sufficient for most processes, while it is generally preferred to employ from 10 to 500 ppmw of metal, and more preferably from 25 to 350 ppmw of metal.

In addition to the metal-organophosphorous ligand complex catalyst, free organophosphorous ligand (i.e., ligand that is not complexed with the metal) may also be present in the reaction medium. The free organophosphorous ligand may correspond to any of the above-defined organophosphorous ligands discussed above. It is preferred that the free organophosphorous ligand be the same as the organophosphorous ligand of the metal-organophosphorous ligand complex catalyst employed. However, such ligands need not be the same in any given process. The hydroformylation process of this invention may involve from 0.1 moles or less to 100 moles or higher of free organophosphorous ligand per mole of metal in the reaction medium. Preferably, the hydroformylation process is carried out in the presence of from 1 to 50 moles of free organophosphorous ligand per mole of metal present in the reaction medium. More preferably, for organopolyphosphites, from 0.1 to 4 moles of free organopolyphosphite ligand are employed per mole of metal. If desired, additional organophosphorous ligand can be supplied to the reaction medium of the hydroformylation process at any time and in any suitable manner, e.g., to maintain a predetermined level of free ligand in the reaction medium.

The hydroformylation process is well known and widely commercially practiced. See, e.g., U.S. Pat. Nos. 4,148,830, 5,237,106, 5,763,679, 5,741,945, 5,767,321, 7,446,231, 7,906,688, and 7,863,487. The reaction conditions of the hydroformylation processes may include any suitable type hydroformylation conditions heretofore employed for producing optically active and/or non-optically active aldehydes. The hydroformylation reaction conditions employed will be governed by the type of aldehyde product desired. For instance, the total gas pressure of hydrogen, carbon monoxide and olefin starting compound of the hydroformylation process may range from 1 to 69,000 kPa. In general, however, it is preferred that the process be operated at a total gas pressure of hydrogen, carbon monoxide and olefin starting compound of less than 14,000 kPa and more preferably less than 3,400 kPa. The minimum total pressure is limited predominately by the amount of reactants necessary to obtain a desired rate of reaction. More specifically, the carbon monoxide partial pressure of the hydroformylation process is preferably from 1 to 6,900 kPa, and more preferably from 21 to 5,500 kPa, while the hydrogen partial pressure is preferably from 34 to 3,400 kPa and more preferably from 69 to 2,100 kPa. In general, the molar ratio of gaseous $H_2$:CO may range from 1:10 to 100:1 or higher, the more preferred molar ratio being from 1:10 to 10:1. In general, the hydroformylation process may be conducted at any operable reaction temperature. Advantageously, the hydroformylation process is conducted at a reaction temperature from −25° C. to 200° C., preferably from 50° C. to 120° C. Advantageously, the reaction temperature is less than 100° C. in the reactor or reaction zone being cooled by the process of the invention.

Newer hydroformylation catalysts (typically based on hydrolyzable organophosphorus ligands) have a higher reaction rate (e.g., greater than 1.5 gmoles aldehyde/liter reactor volume/hour or greater than 2.0 gmoles aldehyde/liter reactor volume/hour) compared to older catalysts. The reaction rates also exhibit complex kinetics (e.g., positive and negative reaction orders with respect to CO). These catalysts typically operate at lower reaction temperatures, e.g., 60 to 80° C., in order to minimize catalyst degradation. The lower operating temperatures result in a lower ΔT between cooling medium and reaction medium, thus reducing heat exchanger heat removal capability. These factors have made designing adequate temperature control systems more complicated than for prior processes using catalysts with slower reaction rates.

It should be understood that the nature of the catalyst is not critical to the invention. Nonetheless, the present invention may be particularly useful for catalysts which exhibit high reactivity (greater than 1.5 gmoles aldehyde/liter reactor volume/hour in the reactor or greater than 2.0 gmoles aldehyde/liter reactor volume/hour in the reactor). As discussed further below, in some embodiments, hydroformylation processes can be useful in converting hydroformylation processes using older to catalysts to processes using newer catalysts having higher reaction rates.

The rate of hydroformylation reaction is a function of catalyst concentration and, in most (but not all) cases, is also a function of olefin concentration. Embodiments of the present invention contemplate reducing the reaction by (1) diverting a portion of an olefin feed stream to a reaction zone downstream from the first reaction zone and changing the olefin partial pressure pressure in the first reaction zone by adjusting the amount of the olefin feed stream that is diverted; and/or (2) diverting a portion of the recycled hydroformylation catalyst to a reaction zone downstream from the first reaction zone and changing the concentration of the catalytic metal in the first reaction zone by adjusting the amount of the recycled hydroformylation catalyst that is diverted. The first approach (option (1)—diverting a portion of the olefin feed) may be most effective when the reaction order of the olefins involved in the hydroformylation reaction is positive order and at least 0.3 in some embodiments, 0.5 or greater in some embodiments, and 0.7 or greater in some embodiments. The lower the reaction order, the less effective the first approach (option (1)) will be. For example, the second approach (option (2)—diverting a portion of the recycled hydroformylation catalyst) may be desirable in cases where the olefin reaction order is below 0.5. In some embodiments, both approaches (option (1) and option (2)) may be implemented. Means to determine reaction kinetics and reaction orders are well known to those of ordinary skill in the art.

It should also be understood that the amount of syngas being fed to each reactor or reaction zone will change but the CO and $H_2$ partial pressures are preferably maintained to insure the N:I ratio (the ratio of normal aldehydes to branched aldehydes produced by the hydroformylation reaction) remains optimal and to insure catalyst stability. The total amount of olefin and syngas fed to the process should not change significantly, just where it is added. Minor changes, if any, in the N:I ratio using the above approaches (option (1) and/or option (2)) to control reaction rate can be compensated for by changing the CO partial pressure or ligand concentration in most cases as will be understood by persons having ordinary skill in the art based on the teachings herein.

The amount of total aldehyde produced ideally will not change significantly using processes according to some embodiments of the present invention, in contrast to conventional methods of controlling over-reactive systems by reducing the total olefin feed. It should be understood that should a slight drop in overall conversion be observed, process parameters in the downstream reaction zones can be altered to increase the conversion in such downstream reactors. Examples of such parameters include the reaction temperature, CO and/or $H_2$ partial pressures, and the like. In general, the amount of reaction occurring in the downstream reaction zones is much less than that of the first reaction zone such that these downstream reaction zones are easier to control using conventional means.

When more than one hydroformylation reactor or reaction zone is used for a given olefin, the hydroformylation reactors or reaction zones downstream of the first reactor or reaction zone in a train may operate at higher reaction rate under some scenarios, but since the amount of available olefin has been greatly reduced by the time the reaction fluid reaches the downstream reactors/zones, the amount of heat being generated is low enough that conventional cooling schemes can be employed for the downstream reactors.

In one embodiment, up to 30% of the total olefin fed to the hydroformylation process is diverted to a downstream reactor to maintain the amount of heat removed in the heat exchanger used to remove heat from the first reaction zone. The diverted olefin is typically fed to the second reactor or reaction zone in the reaction train. In some embodiments, at least 1% of the total olefin fed to the hydroformylation process is diverted to a downstream reactor to maintain the amount of heat removed in the heat exchanger used to remove heat from the first reaction zone. In some embodiments, at least 5% of the total olefin fed to the hydroformylation process is diverted to a downstream reactor to maintain the amount of heat removed in the heat exchanger used to remove heat from the first reaction zone. In some embodiments, at least 10% of the total olefin fed to the hydroformylation process is diverted to a downstream reactor to maintain the amount of heat removed in the heat exchanger used to remove heat from the first reaction zone. In some embodiments, from 1% to 30% of the total olefin fed to the hydroformylation process is diverted to a downstream reactor to maintain the amount of heat removed in the heat exchanger used to remove heat from the first reaction zone. In some embodiments, from 5% to 30% of the total olefin fed to the hydroformylation process is diverted to a downstream reactor to maintain the amount of heat removed in the heat exchanger used to remove heat from the first reaction zone. In some embodiments, from 10% to 30% of the total olefin fed to the hydroformylation process is diverted to a downstream reactor to maintain the amount of heat removed in the heat exchanger used to remove heat from the first reaction zone.

In one embodiment, an existing hydroformylation reaction system can be converted to a system using a more highly reactive catalyst system or a more highly reactive olefin using processes of the present invention. Such conversion can be particularly desirable when the heat exchanger used in the first reactor or first reaction zone designed for the existing hydroformylation system does not have sufficient heat removal capability if a more reactive catalyst system and/or olefin were used instead. By diverting a portion of the olefin and/or catalyst to the second reactor/reaction zone according to processes of the present invention, the overall heat load is redistributed such that the first reactor heat exchanger is capable of handling the heat load. Controlling the ratio of the diverted flows allows stable control of such a retrofit system.

Both approaches (diverting a portion of the olefin feed stram and diverting a portion of the recycled hydroformylation catalyst) can balance the needs of the first reactor or reaction zone for reactivity control so as to avoid excessive temperature, thermal cycling, and similar control problems. For example, with monophosphite based catalyst systems, excessive reaction may lead to CO depletion which may result in rhodium loss. The ability to adjust reactivity in the first reactor by increasing reactivity in the second reactor may allow time to make other adjustments such as lowering the temperature of the first reactor but these alternative processes may be slow and limited by cooling water constraints.

Option (1) (diverting a portion of the olefin feed stream) may have faster response time for control of the first reactor and may be simpler to implement, in some embodiments (i.e., propylene (or other olefin) feed bypass can be adjusted based on temperature in the first reactor or reaction zone without having to measure rhodium content). One possible approach is to monitor the first reactor heat exchanger control valve and as it approaches 90% open, divert a portion of the olefin feed stream and/or a portion of the hydroformylation catalyst recycle stream to reduce reaction (heat load) in the first reactor. In effect, this can act as an "emergency valve". Because too much reaction is occurring in the first reactor, there is little olefin left to react in the second reactor and thus shifting reaction from the overloaded first reactor to the underutilized second reactor will not impact overall conversion.

Option (2) (diverting a portion of the recycled hydroformylation catalyst) may have an advantage in that the rhodium content can be much higher in the downstream reactor than in the first reactor, thus allowing for a more forced reactivity to increase (or at least maintain) overall conversion. Because the residence time from the second reactor to the product/catalyst separation zone, in some embodiments, is shorter than starting from the first reactor, the amount of catalyst degradation generated at the higher concentration may be mitigated by the shorter contact time. Option (2) may be simply implemented using the ratio of flow control of vaporizer tails being supplied to the first reactor and downstream reactor, or by using on-line rhodium measurement techniques (e.g., XRF, GC (e.g., for triarylphosphine-based systems), or HPLC techniques).

It is to be understood than any combination of the above embodiments can be used.

Hydroformylation processes of the present invention can be implemented using process control hardware and software that are readily commercially available, as is known to those skilled in the art in view of the teachings herein. The improved reactor control and stability of the process of the invention provides a useful basis for the effective implementation of Advanced Process Control (APC) techniques such as Multi-variable Model Predictive Control (MMPC), Dynamic Matrix Control (DMC), Real Time Optimization (RTO) or Advanced Control and Optimization (AC&O). Advanced Process Control techniques are well to known those of ordinary skill in the art and can be implemented using techniques known to those of ordinary skill in the art based on the teachings herein.

Any suitable process equipment can be employed. The design and construction, including selection of suitable materials of construction, of hydroformylation process equipment is well known to those skilled in the art. In one embodiment of the invention, the heat exchanger in the first reactor or reaction zone is capable of removing at least 75 $kW/m^3$ of reactor volume from the stream.

Compared to prior art processes, some embodiments of hydroformylation processes of the invention can provide a more rapid response to reaction rate changes. Compared to the prior art, for example, if an increased reactor temperature is detected, decreasing the flow of either recycled catalyst or fresh olefin feed to the first reactor can rapidly reduce the reaction rate. The catalyst or olefin diverted to the second reaction zone will maintain the overall plant production rate.

Some embodiments of the invention will now be described in more detail in the following Examples.

EXAMPLES

All parts and percentages in the following examples are by weight unless otherwise indicated. Pressures are given as absolute pressure unless otherwise indicated.

The following examples are given to illustrate the invention and should not be construed as limiting its scope.

Comparative Example A ("CEA") (not an Embodiment of the Invention)

To illustrate the operation of a conventional hydroformylation reactor control scheme, a simulation is conducted. The process flow sheet shown in FIG. 1 is the basis for this simulation. The reaction rate is modelled with a highly reactive hydroformylation catalyst (a commonly used bisphosphite) and propylene. The kinetics of the catalyst are determined by conventional means analogous to the technique taught in Rush, et. al., "Kinetics and Mechanism of propylene hydroformylation catalyzed by rhodium complexes with a diphosphate Ligand", *Kinetics and Catalysis,* 2009, Vol 50 (#4) pg 557-566. A three reactor train is used for the model and the reaction parameters are given in Table 1 (CEA) for a steady-state, stable operation using AspenPlus Dynamics software, which is commercially available AspenTech. Typical initial process conditions used in the model are given in Table 1.

The effect of changes taught in the present invention are then illustrated in Inventive Examples 1-4 (IE1-4) using the same system as CEA (except as noted below), and the heat load and overall olefin conversion are given without any other optimization. The total amount of olefin feed is kept constant to assess any change in overall plant conversion (measured as "Stabilizer tails" which represents the crude aldehyde product after removing unreacted syngas, olefin, and hydrocarbons).

Inventive Example 1 (IE1)

Figure 2:
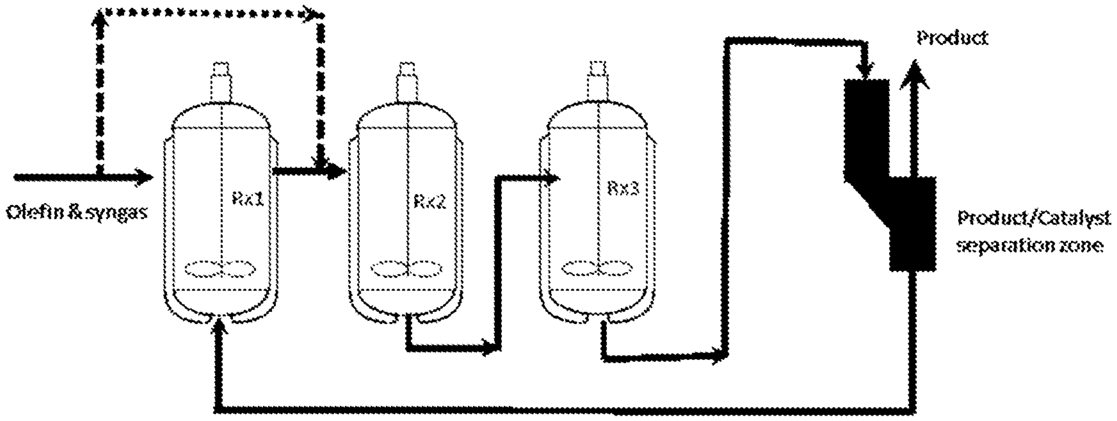
FIG. 2 is a process flow sheet that shows diverting a portion of the olefin feed from a first reactor (reaction zone) to a second reactor (reaction zone) to adjust or control the amount of reaction occurring in the first reactor in accordance with one embodiment of the present invention.

The same parameters used in CEA are used except 10% of the propylene (C3H6) feed is diverted to the second reactor. This diversion of a portion of the propylene feed to the second reactor is shown by the process flow sheet of FIG. 2. Reactor temperatures and syngas partial pressures are kept as constant as possible.

Inventive Example 2 (IE2)

Figure 3:
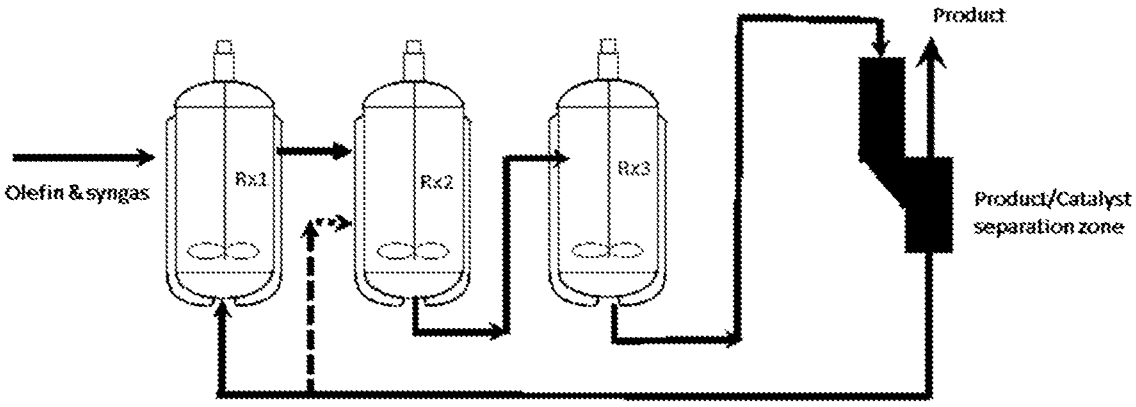
FIG. 3 is a process flow sheet that shows diverting a portion of the recycled catalyst from the product/catalyst separation zone from a first reactor (reaction zone) to a second reactor (reaction zone) to change the catalyst concentration in the first reactor and thus control the amount of reaction occurring in the first reactor in accordance with one embodiment of the present invention.

The same parameters used in CEA are used except 25% of the recycled catalyst from the product/catalyst separation zone is diverted to the second reactor. This diversion of a portion of the recycled catalyst to the second reactor is shown by the process flow sheet of FIG. 3, with the same process flow sheet also being used for Inventive Examples 3 and 4 below. Reactor temperatures and syngas partial pressures are kept as constant as possible.

Inventive Example 3 (IE3)

The same parameters used in CEA are used except 50% of the recycled catalyst from the product/catalyst separation zone is diverted to the second reactor. Reactor temperatures and syngas partial pressures are kept as constant as possible.

Inventive Example 4 (IE4)

The same parameters used in CEA are used except 80% of the recycled catalyst from the product/catalyst separation zone is diverted to the second reactor. Reactor temperatures and syngas partial pressures are kept as constant as possible.

TABLE 1

| | | CEA Base case | IE1 10% C3H6 to R2 | IE2 25% Vap Tails to R2 | IE3 50% Vap Tails to R3 | IE4 80% Vap Tails to R2 |
|---|---|---|---|---|---|---|
| Rx Volumes | | | | | | |
| R1 | $m^3$ | 100 | 100 | 100 | 100 | 100 |
| R2 | $m^3$ | 100 | 100 | 100 | 100 | 100 |
| R3 | $m^3$ | 100 | 100 | 100 | 100 | 100 |
| Rx Temps | | | | | | |
| R1 | C. | 70 | 70 | 70 | 70 | 70 |
| R2 | C. | 70 | 70 | 70 | 70 | 70 |
| R3 | C. | 70 | 70 | 70 | 70 | 70 |
| Rx Rh | | | | | | |
| R1 | ppmw | 70 | 70 | 57.3 | 42.0 | 19.1 |
| R2 | ppmw | 70 | 70 | 76.4 | 84.0 | 95.5 |
| R3 | ppmw | 70 | 70 | 76.4 | 84.0 | 95.5 |
| Total Rh in System | kg | 15.8 | 15.8 | 15.8 | 15.8 | 15.8 |
| Feeds | | | | | | |
| R1 Propylene 95% | kg/hr | 21388 | 19249 | 21388 | 21388 | 21388 |
| R2 Propylene 95% | kg/hr | 0 | 2139 | 0 | 0 | 0 |
| R1 Syngas | kg/hr | 12792 | 11666 | 12428 | 11701 | 8759 |
| R2 Syngas | kg/hr | 1859 | 2834 | 2191 | 2843 | 5408 |
| R3 Syngas | kg/hr | 305 | 434 | 338 | 409 | 752 |
| R1 Partial Pressures | | | | | | |
| H2 | bar | 2.3 | 2.3 | 2.3 | 2.2 | 2.1 |
| CO | bar | 2.1 | 2.1 | 2.1 | 2.1 | 2.1 |
| C3H6 | bar | 3.6 | 3.3 | 4.3 | 5.4 | 7.7 |
| R2 Partial Pressures | | | | | | |
| H2 | bar | 2.3 | 2.3 | 2.4 | 2.4 | 2.3 |
| CO | bar | 2.1 | 2.1 | 2.1 | 2.1 | 2.1 |
| C3H6 | bar | 0.6 | 0.8 | 0.6 | 0.8 | 1.4 |
| R3 Partial Pressures | | | | | | |
| H2 | bar | 2.3 | 2.3 | 2.3 | 2.3 | 2.3 |
| CO | bar | 2.1 | 2.1 | 2.1 | 2.1 | 2.1 |
| C3H6 | bar | 0.1 | 0.1 | 0.1 | 0.1 | 0.2 |
| Ald. Formation Rate | | | | | | |
| R1 | gmol/L/hr | 3.97 | 3.63 | 3.86 | 3.55 | 2.31 |
| R2 | gmol/L/hr | 0.62 | 0.91 | 0.75 | 1.00 | 2.12 |
| R3 | gmol/L/hr | 0.09 | 0.13 | 0.10 | 0.12 | 0.23 |
| Overall | gmol/L/hr | 1.56 | 1.56 | 1.57 | 1.56 | 1.55 |
| Rx Duty | | | | | | |
| R1 | MW | −16.3 | −14.9 | −15.8 | −14.7 | −9.3 |
| R2 | MW | −2.5 | −3.7 | −3.0 | −4.0 | −8.8 |
| R3 | MW | −0.4 | −0.5 | −0.4 | −0.5 | −1.0 |
| % Duty shift | | | 9% | 3% | 10% | 43% |
| Stabiliser Tails | kg/hr | 33930 | 33873 | 33929 | 33919 | 33826 |
| C3 to Ald | % | 97.4% | 97.2% | 97.4% | 97.4% | 97.1% |

Inventive Example 1 shows that diverting 10% of the olefin (propylene) to the second reactor gave nearly the same decrease in duty on the first reactor heat exchanger (9%) with a very small decline in overall plant conversion (97.2% relative to CEA's 97.4%). The small decline in overall plant conversion could be easily rectified, for example, by a slight increase in process parameters in a downstream reactor such as syngas partial pressures or temperature.

Inventive Examples 2-4 show that large shifts in the amount of recycled catalyst being diverted to the second reactor gave modest shifts in reactor load in the first reactor. The amount of reaction does not change in a linear fashion because while the catalyst concentration is dropping, the resulting unconverted olefin concentration goes up such that the two effects partially cancel out. This means that adjusting the amount of recycled catalyst provided to the first reactor (diverted to the second reactor) allows modest and controlled shifts of reactivity (and thus duty shift) in the first reactor. Shifting 50% of the recycled catalyst (Inventive Example 3) gave no detectable change in plant productivity but gave a comparable amount of control (10% reduction in heat duty in the first reactor) as seen in Inventive Example 1. Even diverting 80% of the recycled catalyst to the second reactor (Inventive Example 4) to give a 43% reduced duty on the first reactor only gave a 0.3% drop in overall plant conversion. The small decline in overall plant conversion could be easily rectified, for example, by a slight increase in process parameters in downstream reactor such as syngas partial pressures or temperature.

What is claimed is:

1. A continuous hydroformylation process comprising (a) contacting CO, $H_2$, and at least one olefin in the presence of a hydroformylation catalyst in a reaction fluid in at least two reaction zones under hydroformylation conditions sufficient to form at least one aldehyde product, wherein the hydroformylation catalyst comprises a catalytic metal and a ligand and wherein a reaction temperature in the first reaction zone is controlled using a first heat exchanger; and (b) recovering at least a portion of the hydroformylation catalyst from a product stream and recycling at least a portion of the recovered hydroformylation catalyst through the first reaction zone;

wherein the heat evolution in the first reaction zone is reduced by reducing the reaction rate in the first reaction zone and increasing the reaction rate in a downstream reaction zone to insure sufficient heat removal capacity remains on the heat exchanger in the first reaction zone to insure stable control of the reaction at a target reaction temperature by: (1) diverting a portion of an olefin feed stream to a reaction zone downstream from the first reaction zone and changing the olefin partial pressure pressure in the first reaction zone by adjusting the amount of the olefin feed stream that is diverted; and/or (2) diverting a portion of the recycled hydroformylation catalyst to a reaction zone downstream from the first reaction zone and changing the concentration of the catalytic metal in the first reaction zone by adjusting the amount of the recycled hydroformylation catalyst that is diverted.

2. The process of claim 1, wherein the reaction temperature in the first reaction zone is maintained within 1° C. of the target reaction temperature.

3. The process of claim 1, further comprising measuring the olefin concentration in a headspace of the first reaction zone and adjusting the amount of the olefin feed stream diverted to the downstream reaction zone based on the measurement.

4. The process of claim 1 wherein the reaction rate in the first reaction zone is greater than 1.5 gmoles aldehyde/liter reactor volume/hour.

5. The process of claim 1 wherein the ligand is a hydrolyzlable organophosphorus ligand.

6. The process of claim 1 wherein the catalytic metal is rhodium.

7. The process of claim 1, wherein the reaction temperature is 100° C. or less.

8. The process of claim 1 wherein at least one Advanced Process Control technique is employed to control the hydroformylation process.

* * * * *